(12) United States Patent
Dedhiya et al.

(10) Patent No.: US 8,247,400 B2
(45) Date of Patent: Aug. 21, 2012

(54) CEPHEM COMPOUNDS USEFUL FOR THE TREATMENT OF BACTERIAL INFECTIONS

(76) Inventors: Mahendra G. Dedhiya, Pomona, NY (US); Brahma N. Singh, Syosset, NY (US)

( * ) Notice: Subject to any disclaimer, the term of this patent is extended or adjusted under 35 U.S.C. 154(b) by 352 days.

(21) Appl. No.: 12/710,417

(22) Filed: Feb. 23, 2010

(65) Prior Publication Data

US 2010/0216745 A1     Aug. 26, 2010

Related U.S. Application Data

(60) Provisional application No. 61/154,455, filed on Feb. 23, 2009.

(51) Int. Cl.
*C07D 501/59* (2006.01)
*A61K 31/546* (2006.01)
*A61P 31/04* (2006.01)

(52) U.S. Cl. .................................. 514/203; 540/225

(58) Field of Classification Search .............. 540/225; 514/203
See application file for complete search history.

(56) References Cited

U.S. PATENT DOCUMENTS

| 4,254,119 | A | 3/1981 | Hamashima et al. |
| 5,409,919 | A | 4/1995 | Miyake et al. |
| 6,417,175 | B1 | 7/2002 | Ishikawa et al. |
| 6,906,055 | B2 | 6/2005 | Ishikawa et al. |
| 2011/0152311 | A1* | 6/2011 | Dedhiya et al. ............... 514/300 |

OTHER PUBLICATIONS

International Search Report for corresponding International Application No. PCT/US2010/25006, mailed Apr. 8, 2010.
Written Opinion of the International Searching Authority for corresponding International Application No. PCT/US2010/25006, mailed Apr. 8, 2010.
Talbot et al. Phase 2 Study of Ceftaroline versus Standard Therapy in Treatment of Complicated Skin and Skin Structure Infections. Antimicrobial Agents and Chemotherapy, 2007, vol. 51, No. 10, pp. 3612-3616, para 9 to p. 3614, para 3; Table 2; p. 3615, para 6 to p. 3616, para 1.
Ikeda et al. Stability and Stabilization Studies of TAK-599 (Ceftaroline Fosamil), a Novel N-Phosphono type Prodrug of Antimethicillin Resistant *Staphylococcus aureus* Cephalosporin T-91825. Chem. Pharm. Bull., 2008, vol. 56(10), pp. 1406-1411; p. 1406, para 3, para 5.
Developing Antimicrobial Drugs—General Considerations for Clinical Trials, U.S. Department of Health and Human Services, Food and Drug Administration, Draft Guidance for Industry, Jul. 1998.

* cited by examiner

*Primary Examiner* — Mark Berch

(57) ABSTRACT

The present invention relates to new cephem compounds useful for the treatment of bacterial infections of formula I:

The invention also relates to methods of preparing the compounds, pharmaceutical compositions comprising the compounds, and to methods of treatment using the compounds. The new cephem compounds are stable, exhibit good solubility, and are particularly well suited for, e.g., parenteral administration for the treatment of bacterial infections.

23 Claims, 1 Drawing Sheet

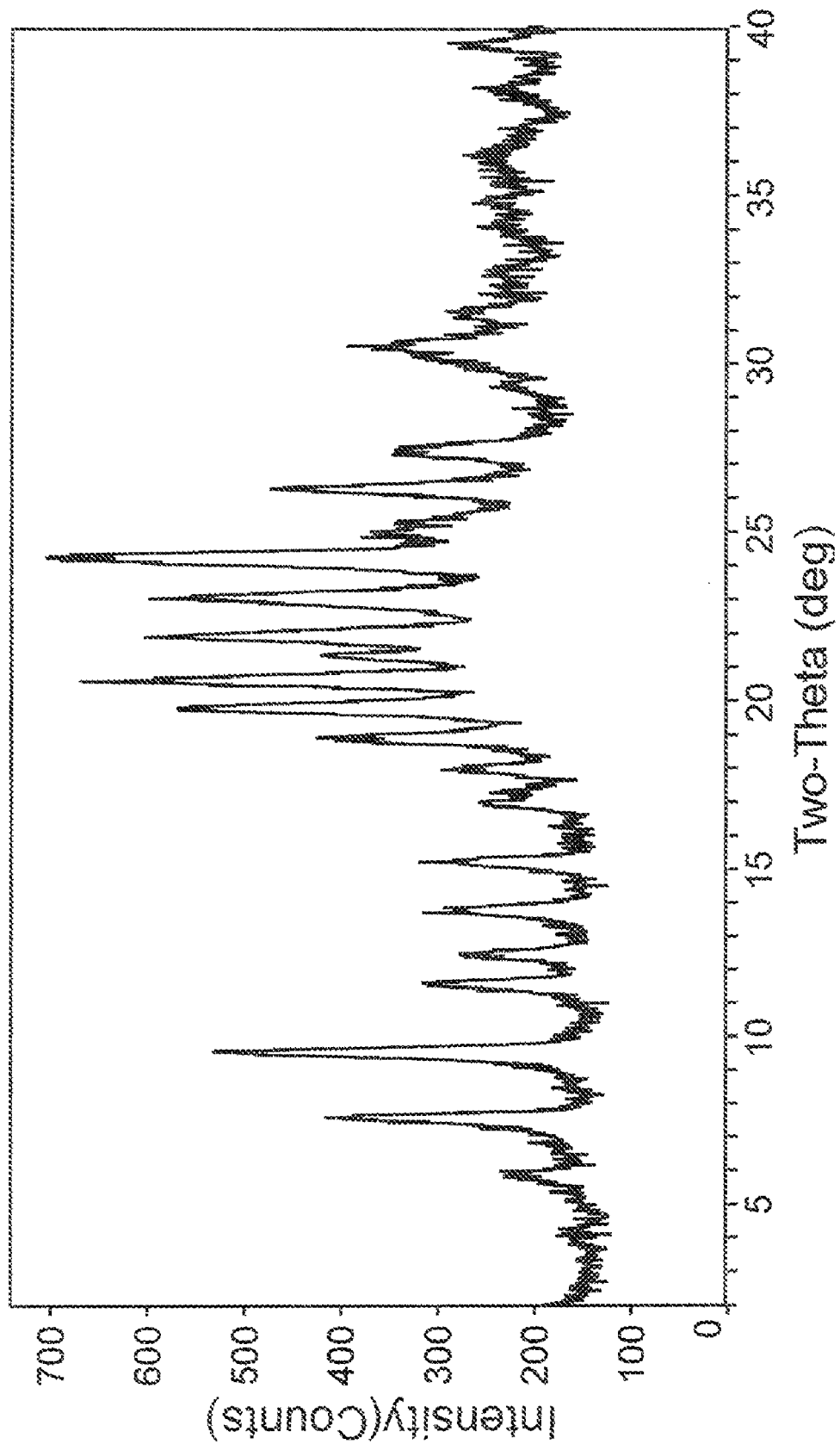

CEPHEM COMPOUNDS USEFUL FOR THE TREATMENT OF BACTERIAL INFECTIONS

CROSS REFERENCE TO RELATED APPLICATIONS

This application claims priority under 35 U.S.C. §119, based on U.S. Provisional Application Ser. No. 61/154,455 filed on Feb. 23, 2009, which is hereby incorporated by reference in its entirety.

FIELD OF THE INVENTION

The present invention relates to new cephem compounds useful for the treatment of bacterial infections. The invention also relates to methods of preparing the compounds, pharmaceutical compositions containing the compounds, and to methods of treatment using the compounds. The new cephem compounds are stable, exhibit good solubility, and are particularly well suited for, e.g., parenteral administration for the treatment of bacterial infections.

BACKGROUND OF THE INVENTION

U.S. Pat. No. 6,417,175 discloses phosphonocephem derivatives having excellent antibacterial activities for a broad range of Gram-positive and Gram-negative bacteria. These compounds are of the general formula:

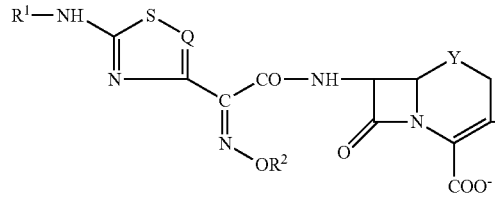

wherein $R^1$-$R^4$, Q, X, Y and n are as defined therein. One such compound is 7β-[2(Z)-ethoxyimino-2-(5-phosphonoamino-1,2,4-thiadiazol-3-yl)acetamido]-3-[4-(1-methyl-4-pyridinio)-2-thiazolylthio]-3-cephem-4-carboxylate (molecular formula $C_{22}H_{21}N_8O_8PS_4$, molecular weight 684.68). The 2008 proposed International Nonproprietary Name (INN) for this compound is ceftaroline fosamil.

U.S. Pat. No. 6,906,055 discloses compounds of formula:

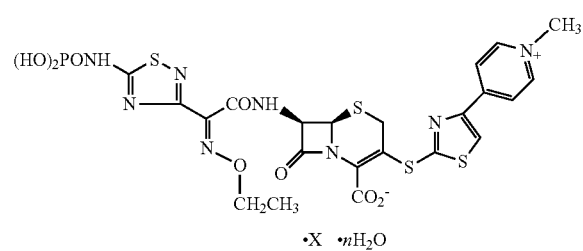

in which X is $CH_3COOH$, $CH_3CH_2COOH$ or $CH_3CN$ and n is 0-5. One such compound (where X is $CH_3COOH$ and n is 1) is (6R,7R)-7-[[2(Z)-ethoxyimino-[5-(phosphonoamino)-1,2,4-thiadiazol-3-yl]acetyl]amino]-3-[[4-(1-methyl-pyridinium-4-yl)thiazol-2-yl]sulfanyl]-8-oxo-5-thia-1-azabicyclo[4.2.0]oct-2-en-2-carboxylate monoacetate monohydrate, which is also known as pyridinium, 4-[2-[[(6R,7R)-2-carboxy-7-[[2(Z)-ethoxyimino-[5-(phosphonoamino)-1,2,4-thiadiazol-3-yl]acetyl]amino]-8-oxo-5-thia-1-azabicyclo[4.2.0]oct-2-en-3-yl]thio-4-thiazolyl]-1-methyl-, inner salt, monoacetate, monohydrate (molecular formula $C_{22}H_{21}N_8O_8PS_4 \cdot C_2H_4O_2 \cdot H_2O$, molecular weight 762.75). The 2006 published USAN name for this compound is ceftaroline fosamil acetate.

When administered, compounds such as ceftaroline fosamil and ceftaroline fosamil acetate are converted in body fluids into the active antibacterial moiety ceftaroline.

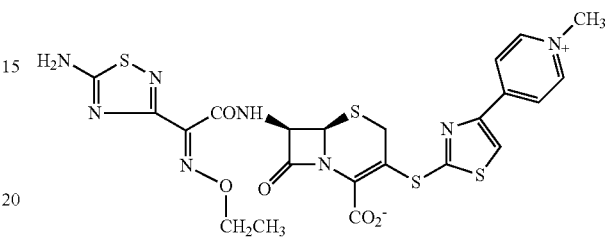

Gram-positive bacterial pathogens have revealed an extraordinary ability to develop resistance to antimicrobial agents in the last two decades. Thus, there is a clinical need for new broad-spectrum antimicrobial agents that covers both resistant gram-positive and gram-negative pathogens. Applicants have developed novel cephem compounds that are stable, exhibit good solubility, and are particularly well suited for, e.g., parenteral administration for the treatment of gram-positive and gram-negative bacterial infections.

SUMMARY OF THE INVENTION

The present invention relates to new cephem compounds useful for the treatment of bacterial infections. The invention also relates to methods of preparing the compounds, pharmaceutical compositions containing the compounds, and to methods of treatment using the compounds. The new cephem compounds are stable, exhibit good solubility, and are particularly well suited for, e.g., parenteral administration for the treatment of bacterial infections.

According to some embodiments, the present invention provides (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate or a pharmaceutically acceptable salt thereof and compositions comprising (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate or a pharmaceutically acceptable salt thereof.

According to some embodiments, the present invention provides methods of treating bacterial infections, e.g., community acquired pneumonia, complicated skin and skin structure infections and complicated urinary tract infection in a patient in need thereof comprising administering a composition comprising (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate or a pharmaceutically acceptable salt thereof.

BRIEF DESCRIPTION OF THE DRAWINGS

FIG. 1 shows the X-ray powder diffraction pattern of (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate hydrochloride.

DETAILED DESCRIPTION OF THE INVENTION

In one aspect, the present invention includes compounds of formula I:

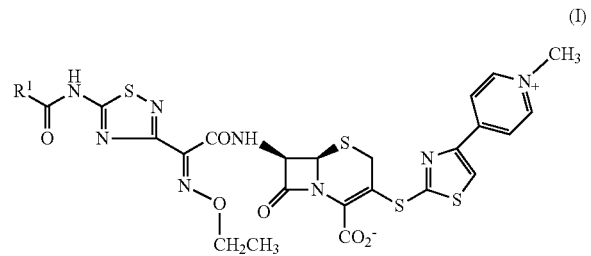

(I)

wherein
$R^1$ is hydrogen, alkyl, alkenyl, alkynyl, aryl, heteroaryl, heterocycle, —C(O)alkyl, —C(O)OH, —CH(NH$_2$)(CH$_2$)$_3$—NH—C(NH)NH$_2$ or —CH(NH$_2$)—CH$_2$—C(O)NH$_2$;

wherein, when present, any alkyl, aryl, heteroaryl or heterocycle group may optionally be substituted by halogen, hydroxyl, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, thio, alkylthio, arylthio, alkylsulfinyl, alkylsulfonyl, arylsulfinyl, arylsulfonyl, heteroarylsulfinyl, heteroarylsulfonyl, alkoxycarbonyl, aryloxycarbonyl, heteroaryloxycarbonyl, and combinations thereof;

and pharmaceutically acceptable salts (e.g., hydrochloride) or solvates (e.g., acetate, hydrate), or solvates of pharmaceutically acceptable salts thereof.

In certain embodiments, $R^1$ is hydrogen, alkyl, alkenyl, alkynyl, aryl, heteroaryl or heterocycle.

In certain embodiments, $R^1$ is hydrogen, alkyl or aryl. For example $R^1$ is hydrogen or alkyl. For further example, $R^1$ is hydrogen or methyl.

In additional embodiments, $R^1$ is hydrogen, —CH$_3$, —CH$_2$CH$_3$, —(CH$_2$)$_2$CH$_3$, —(CH$_2$)$_3$CH$_3$, —(CH$_2$)$_4$CH$_3$, —(CH$_2$)$_5$CH$_3$, —(CH$_2$)$_6$CH$_3$, —(CH$_2$)$_7$CH$_3$, —(CH$_2$)$_8$CH$_3$, —(CH$_2$)$_{10}$CH$_3$, —(CH$_2$)$_{16}$CH$_3$, —CH=CH$_2$, —C(O)CH$_3$, phenyl, 2-hydroxyphenyl, —C(O)OH, —CH$_2$C(O)OH, —(CH$_2$)$_2$C(O)OH, —(CH$_2$)$_3$C(O)OH, —(CH$_2$)$_4$C(O)OH, —CH(OH)—CH$_2$C(O)OH, —CH$_2$—C(O)(CO$_2$H)—CH$_2$—C(O)OH, —CH(OH)CH$_3$, —CH(NH$_2$)CH$_3$, —CH(NH$_2$)(CH$_2$)$_3$—NH—C(=NH)NH$_2$, —CH(NH$_2$)—CH$_2$—C(O)NH$_2$, —CH(NH$_2$)—CH$_2$—C(O)OH or —CH(NH$_2$)—CH$_2$SH.

In exemplary embodiments, $R^1$ is methyl, ethyl, n-propyl, i-propyl, n-butyl, i-butyl, t-butyl or n-pentyl. For example, $R^1$ is methyl, ethyl or n-propyl. In an exemplary embodiment, $R^1$ is methyl. In another embodiment, $R^1$ is hydrogen.

In other embodiments, $R^1$ is aryl (e.g., phenyl, hydroxyphenyl).

In certain embodiments, the compound of formula I is selected from:
(6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate,
(6R,7R)-7-[[(2Z)-2-(ethoxyimino)-2-[5-(amido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate,
(6R,7R)-7-[[(2Z)-2-(ethoxyimino)-2-[5-(ethylamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate, and
(6R,7R)-7-[[(2Z)-2-(ethoxyimino)-2-[5-(n-propylamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate, wherein free base forms listed above can also be in the form of a pharmaceutically acceptable salt, wherein a compound listed above (in either a free base form or in the form of a pharmaceutically acceptable salt) can also be in the form of a solvate (such as an acetate and/or a hydrate).

In an exemplary embodiment, the compound of formula I is (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate, or a pharmaceutically acceptable salt and/or solvate thereof.

(6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2ene-2-carboxylate is also referred to herein as "Compound A."

In a further exemplary embodiment, the compound of formula (I) is (6R,7R)-7-[[(2Z)-2-(ethoxyimino)-2-[5-(acetamido)-1,2,4-thiadiazol-3-yl]acetyl]amino]-3-[[4-(1-methylpyridini-1-ium-4-yl)-1,3-thiazol-2-yl]sulfanyl]-8-oxo-5-thia-1-azabicylo[4.2.0]oct-2-ene-2-carboxylate hydrochloride (Compound A hydrochloride).

In another exemplary embodiment, the compound of formula (I) is (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate acetate (Compound A acetate).

In one embodiment, the present invention also provides a crystalline form of (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate hydrochloride] characterized by a X-ray powder diffraction pattern comprising a characteristic peak at about 7.6, about 9.6, about 19.8, about 20.6, about 21.9, about 23.0 or about 24.3±0.2 degrees 2θ.

In exemplary embodiments, the present invention provides a crystalline form of (6R,7R)-7-[[(2Z)-2-(ethoxyimino)-2-

[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate hydrochloride] characterized by a X-ray powder diffraction pattern comprising one or more characteristic peaks at about 7.6, about 9.6, about 19.8, about 20.6, about 21.9, about 23.0 and about 24.3±0.2 degrees 2θ.

In another embodiment, the present invention also provides a crystalline form of (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate hydrochloride] characterized by a X-ray powder diffraction pattern comprising characteristic peaks at about 9.6, about 20.6, about 21.9, about 23.0 and about 24.3±0.2 degrees 2θ.

In another embodiment, the present invention also provides a crystalline form of (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate hydrochloride] characterized by a X-ray powder diffraction pattern comprising characteristic peaks at about 7.6, about 9.6 and about 24.3±0.2 degrees 2θ.

In another embodiment, the present invention also provides a crystalline form of (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate hydrochloride] characterized by a X-ray powder diffraction pattern comprising characteristic peaks at about 9.6, about 20.6 and about 24.3±0.2 degrees 2θ.

In a further embodiment, the crystalline form of (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate hydrochloride is characterized by a X-ray powder diffraction pattern substantially as shown in FIG. 1.

With respect to the term "substantially," one skilled in the art would understand that the relative intensities of the peaks can vary, depending upon the sample preparation technique, the sample mounting procedure and the particular instrument employed. Moreover, instrument variation and other factors can affect the 2θ values. Therefore, the XRD peak assignments can vary by plus or minus about 0.2 degrees 2θ.

Compounds of Formula I may be prepared according to the following general reaction scheme:

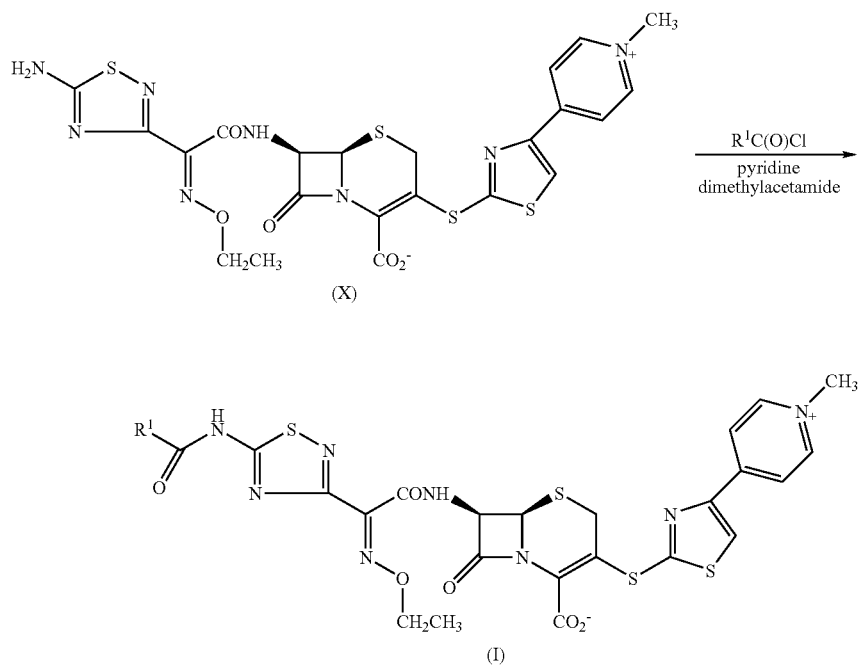

Compound X may be reacted with a suitable acid (e.g., acetic acid) or acid halide (e.g., acetyl chloride) and a base (such as pyridine) in the presence of a suitable solvent (e.g., dimethylacetamide) to afford a compound of formula (I). A wide variety of compounds of formula I may be prepared using appropriately substituted acids or acid halides (e.g., $R^1$=H, Me, Et, n-Pr, phenyl, and the like).

Suitable acids that may be used include, for example, formic acid, acetic acid, propionic acid, butyric acid, valeric acid, caproic acid, enanthic acid, caprylic acid, pelargonic acid, capric acid, lauric acid, stearic acid, acrylic acid, docosahexaenoic acid, eicosapentaenoic acid, pyruvic acid, benzoic acid, salicylic acid, oxalic acid, malonic acid, succinic acid, glutaric acid, adipic acid, citric acid, lactic acid, aspartic acid, alanine, arginine, aspargine, cysteine and the like. Suitable acid halide derivatives of the above acids may also be used.

Pharmaceutical Compositions

In additional aspects, the present invention relates to pharmaceutical compositions comprising a compound of formula I (e.g., Compound A) or a pharmaceutically acceptable salt and/or solvate and/or prodrug thereof, and a pharmaceutically acceptable carrier.

Examples of suitable pharmaceutical compositions comprising Compound A hydrochloride are given in Tables 1 and 2.

TABLE 1

Pharmaceutical Compositions Containing Compound A Hydrochloride

| Ingredient | Range (mg) | Example* (amount per 120 ml) |
|---|---|---|
| Compound A hydrochloride | 160-1660 | 558 mg** |
| Propylene Glycol, USP | 8.0-86.0 | 28.8 ml |
| Ethanol 95%, USP | 2.0-21.5 | 7.2 ml |
| PEG-300, USP/NF | 10.0-107.0 | 36. ml |
| Acetate Buffer (pH 5.0, 1M) | 14.0-143.0 | q.s. to 120 ml |

*concentration of Compound A is 4.20 mg/ml
**corrected for purity (factor of 0.95) and free base/HCl salt ratio (factor of 0.95)

TABLE 2

Pharmaceutical Compositions Containing Compound A Hydrochloride and L-Arginine

| Ingredient | Range (mg) | Example* (mg/batch) |
|---|---|---|
| Compound A hydrochloride | 2-30 | 27.6 |
| L-arginine | 39-588.5 | 543.3 |
| Normal saline for injection, USP | 1.5-25.0 | q.s. to 25 ml |
| 0.5 N HCl | 0-2 ml | q.s. |

*concentration of Compound A is 1 mg/ml
**corrected for purity (factor of 0.95) and free base/HCl salt ratio (0.95)

In additional aspects, the present invention relates to pharmaceutical compositions comprising (i) a compound of formula I (e.g., Compound A) or a pharmaceutically acceptable salt and/or solvate and/or prodrug thereof, (ii) ceftaroline, or a pharmaceutically acceptable salt and/or solvate and/or prodrug thereof (e.g., ceftaroline, ceftaroline fosamil, ceftaroline fosamil acetate) and a pharmaceutically acceptable carrier.

Examples of exemplary pharmaceutical compositions containing Compound A and ceftaroline fosamil are given in Table 3.

TABLE 3

Pharmaceutical Compositions Containing Compound A and Ceftaroline Fosamil

| Ingredient | Range (mg) | Example 1 (mg) | Example 2 (mg) | Example 3 (mg) | Example 4 (mg) |
|---|---|---|---|---|---|
| Ceftaroline fosamil[a] | 200-1200 mg | 600 mg | 600 mg | 600 mg | 600 mg |
| L-Arginine | 50-750 mg | 440 mg | 440 mg | 440 mg | 440 mg |
| Compound A | 5-45 mg | 6 mg | 15 mg | 18 mg | 45 mg |
| Normal saline for injection, USP | 20 ml | 20 ml | 20 ml | 20 ml | 20 ml |

[a]A dose of about 600 mg of ceftaroline fosamil (INN) is equivalent to a dose of about 668 mg of ceftaroline fosamil acetate (USAN) which is equivalent to a dose of about 530 mg of ceftaroline The pharmaceutical compositions may be prepared, for example, by mixing the active agent(s) with suitable excipients, for example, DL arginine, L-arginine, propylene glycol, ethanol, PEG, etc., and combinations thereof, in a blender under sterile conditions until a uniform blend is obtained. Pre-sterilized vials may then be filled with an appropriate amount of the sterile blend. The predetermined amount of sterile blend may then be mixed with a solvent, e.g., water, saline, about 5-10% sugar (e.g., glucose, dextrose) solution and combinations thereof prior to administration. In addition, the solution may be frozen and thawed prior to further processing.

In certain embodiments, the compound of formula I, or a pharmaceutically acceptable salt and/or solvate thereof may be administered in a daily dose ranging from about 0.5 mg/kg to about 400 mg/kg, such as from about 2 mg to 40 mg/kg of body weight. In still other embodiments, the daily dose may range from about 5 to about 30 mg/kg of body weight. In exemplary embodiments, a compound of formula I, or a pharmaceutically acceptable salt and/or solvate thereof may be administered in a dose of about 1 mg, about 2.5 mg, about 5 mg, about 6 mg, about 7.5 mg, about 10 mg, about 15 mg, about 18 mg, about 20 mg, about 30 mg, about 40 mg, about 50 mg, about 75 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg or about 1800 mg per day. For example, a compound of formula I, or a pharmaceutically acceptable salt and/or solvate thereof, may be administered in a dose of about 6 mg, about 15 mg or about 18 mg per day.

In further embodiments, compound I, or a pharmaceutically acceptable salt and/or solvate thereof and ceftaroline, or a pharmaceutically acceptable salt and/or solvate and/or prodrug thereof (e.g., ceftaroline fosamil) may be administered such that the dose of ceftaroline fosamil ranges from about 1 mg to about 3000 mg per day in single or multiple administrations. In exemplary embodiments, ceftaroline or a pharmaceutically acceptable salt and/or solvate and/or prodrug thereof (e.g., ceftaroline fosamil) may be administered in a dose of about 5 mg, about 6 mg, about 10 mg, about 15 mg, about 18 mg, about 20 mg, about 30 mg, about 40 mg, about 50 mg, about 75 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg or about 1800 mg per day.

For example, ceftaroline fosamil may be administered in a dose of about 200 mg, about 400 mg, about 500 mg, about 600 mg, about 800 mg, about 1000 mg, about 1200 mg or about 1800 mg.

For further example, ceftaroline fosamil acetate may be administered in a dose of about 234 mg, about 446 mg, about 668 mg, about 891 mg, about 1114 mg, about 1337 mg or about 2005 mg.

One will recognize that a dose of about 223 mg ceftaroline fosamil acetate is equivalent to a dose of about 200 mg ceftaroline fosamil which is equivalent to a dose of about 177 mg ceftaroline.

A dose of about 446 mg ceftaroline fosamil acetate is equivalent to a dose of about 400 mg ceftaroline fosamil which is equivalent to a dose of about 353 mg ceftaroline.

A dose of about 557 mg ceftaroline fosamil acetate is equivalent to a dose of about 500 mg ceftaroline fosamil which is equivalent to a dose of about 442 mg ceftaroline.

A dose of about 668 mg ceftaroline fosamil acetate is equivalent to a dose of about 600 mg ceftaroline fosamil which is equivalent to a dose of about 530 mg ceftaroline.

A dose of about 891 mg ceftaroline fosamil acetate is equivalent to a dose of about 800 mg ceftaroline fosamil which is equivalent to a dose of about 706 mg ceftaroline.

A dose of about 1114 mg ceftaroline fosamil acetate is equivalent to a dose of about 1000 mg ceftaroline fosamil which is equivalent to a dose of about 883 mg ceftaroline.

A dose of about 1337 mg ceftaroline fosamil acetate is equivalent to a dose of about 1200 mg ceftaroline fosamil which is equivalent to a dose of about 1060 mg ceftaroline.

A dose of about 2005 mg ceftaroline fosamil acetate is equivalent to a dose of about 1800 mg ceftaroline fosamil which is equivalent to a dose of about 1589 mg ceftaroline.

The pharmaceutical compositions of the present invention, include, but are not limited to, dosage forms such as, tablets (including a sugar-coated tablet, a film-coated tablet), pills, capsules (including microcapsule), granules, fine granules, powders, drop infusions, syrups, emulsions, suspensions, solutions, injections, aerosols, suppositories, troches, cataplasms, ointments, gels, creams, sustained release preparations, etc. These preparations can be prepared by conventional methods. As carriers for injectable preparations, use is made of, for example, distilled wader, a sugar solution or a physiological saline solution. Carriers for capsules, powdery preparations, granular preparations or tablets are used as a mixture with known pharmaceutically acceptable excipients (for example, starch, maltose, sucrose, calcium carbonate or calcium phosphate), binders (for example, starch, gum arabic, carboxymethyl cellulose, hydroxypropyl cellulose or crystalline cellulose), lubricants (for example, magnesium stearate or talc) and disintegrants (for example, carboxymethyl calcium and talc).

In certain embodiments, the compositions may be in the form of a powder to be dissolved extemporaneously in an appropriate vehicle, for example, distilled water, a sugar solution or a physiological saline solution. The active ingredients may be incorporated with the excipients usually used in these pharmaceutical compositions, such as, for example, talc, gum arabic, lactose, starch, magnesium stearate, cocoa butter, aqueous or non aqueous vehicles, fatty matter of animal or vegetable origin, paraffin derivatives, glycols, various wetting, dispersing or emulsifying agents, preservatives.

In other embodiments, the pharmaceutical composition may comprise pharmaceutically acceptable carriers, including, but not limited to, diluents and bulking agents, which are selected from excipients, such as, calcium carbonate, kaolin, sodium hydrogen carbonate, lactose, D-mannitol, starch, crystalline cellulose, talc, fine granulated sugar and porous substance; binders, such as, dextrin, gums, a-starch, gelatin, hydroxypropylcellulose, hydroxy propyl methyl cellulose and pullulan; thickeners such as, natural gum, cellulose derivative, acrylic acid derivative; disintegrators, such as, carboxymethylcellulose calcium, crosscarmelose sodium, crosspovidone, a low-substituted hydroxypropylcellulose and partly pregelatinized starch; solvents such as, water for injection, alcohol, propylene glycol, Macrogol, sesame oil and corn oil; dispersants, such as, TWEEN® 80 (polyoxyethylenesorbitan monooleate), HCO60, polyethylene glycol, carboxymethylcellulose, and sodium alginate; solubilizing agents, such as, polyethylene glycol, propylene glycol, D-mannitol, benzoic acid benzyl, ethanol, tris amino methane, triethanolamine, sodium carbonate, and citric acid sodium; suspending agents, such as, stearyl triethanolamine, sodium lauryl sulfate, benzalkonium chloride, polyvinylalcohol, and polyvinylpyrrolidone, hydroxymethylcellulose; soothing agents, such as, benzyl alcohol; isotonic agents such as, sodium chloride and glycerin; buffer agents, such as, phosphoric acid salt, acetic acid salt, carbonic acid salt and citric acid salt; lubricants, such as, magnesium stearate, calcium stearate, talc, starch and sodium benzoate; coloring agents, such as, tar pigment, caramel, ferric oxide, titanium oxide and riboflavine; corrigents, such as, sweetening agents and perfumes; stabilizers, such as, sodium sulfite and ascorbic acid; and preservatives, such as, paraben and sorbic acid.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), (current edition). The mode of administration and dosage forms is closely related to the therapeutic amounts of the compounds or compositions which are desirable and efficacious for the given treatment application.

Suitable dosage forms include, but are not limited to oral, rectal, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, and intra-uterille administration, and other dosage forms for systemic delivery of active ingredients. To prepare such pharmaceutical dosage fauns, the active ingredient, is intimately admixed with a pharmaceutical carrier according to conventional pharmaceutical compounding techniques. The carrier may take a wide variety of forms depending on the foam of preparation desired for administration.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. If desired, tablets may be sugar coated or enteric coated by standard techniques.

For parenteral formulations, the carrier will usually comprise sterile water, though other ingredients, for example, ingredients that aid solubility or for preservation, may be included. Injectable solutions may also be prepared in which case appropriate stabilizing agents may be employed.

Treatment methods of the present invention using formulations suitable for oral administration may be presented as discrete units such as capsules, cachets, tablets, or lozenges, each comprising a predetermined amount of the active ingredient as a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with, for example, a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration usually comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

The formulations of the present invention can have immediate release, sustained release, delayed-onset release or any other release profile known to one skilled in the art.

In the clinical study of anti-infective drugs, dose selection, dose regimen, and duration of therapy should take into account the biopharmaceutics, pharmacokinetics, and pharmacodynamics of the anti-infective drug/drug product. See e.g., "Developing Antimicrobial Drugs—General Considerations for Clinical Trials," U.S. Department of Health and Human Services, Food and Drug Administration, Draft Guidance for Industry, July 1998.

In one embodiment, the pharmaceutical compositions of the present invention contain a compound of formula I and about 660 mg ceftaroline fosamil acetate. In other embodiments, the pharmaceutical compositions contain a compound of formula I and about 600 mg ceftaroline fosamil.

In further embodiment, the pharmaceutical compositions contain a compound of formula I and about 446 mg ceftaroline fosamil acetate. In yet further embodiments, the pharmaceutical compositions contain a compound of formula I and about 400 mg ceftaroline fosamil.

In additional embodiments, the pharmaceutical compositions contain a compound of formula I and about 223 mg ceftaroline fosamil acetate. In further embodiments, the pharmaceutical composition contains a compound of formula I and about 200 mg ceftaroline fosamil.

Methods of Treatment

In another aspect, the present invention provides methods of treating a bacterial infection in a patient in need thereof, comprising administering to the patient a therapeutically effective amount of a compound of formula I, or a pharmaceutically acceptable salt and/or solvate thereof.

In a further aspect, the present invention provides methods of treating a bacterial infection in a patient in need thereof, comprising administering a therapeutically effective amount of a compound of formula I, or a pharmaceutically acceptable salt and/or solvate and/or prodrug thereof and ceftaroline, or a pharmaceutically acceptable salt and/or solvate and/or prodrug thereof.

In some embodiments, the bacterial infection to be treated may be due to Gram-positive bacteria, including, but not limited to, methicillin resistant *S. aureus* (MRSA), community-acquired methicillin resistant *S. aureus* (CAMRSA), vancomycin-intermediate-susceptible *S. aureus* (VISA), methicillin-resistant coagulase-negative staphylococci (MR-CoNS), vancomycin-intermediate-susceptible coagulase-negative staphylococci (VI-CoNS), methicillin susceptible *S. aureus* (MSSA), *S. pneumoniae* (including penicillin-resistant *Streptococcus pneumoniae* [PRSP]), *S. pyogenes* and *E. faecalis*. In other embodiments, the bacterial infection may be due to Gram-negative bacteria, such as, *E. coli, E. cloacae, E. faecalis, K. pneumoniae, P. aeruginosa, H. influenzae* (including ampicillin-resistant *H. influenzae*), *M. catarrhalis* and *A. baumanii*.

In particular embodiments, the bacterial infection may include, but is not limited to, complicated skin and skin structure infections (cSSSI); community acquired pneumonia (CAP); complicated intra-abdominal infections, such as, complicated appendicitis, peritonitis, complicated cholecystitis and complicated diverticulitis; uncomplicated and complicated urinary tract infections, such as, pyelonephritis; and respiratory and other nosocomial infections.

In some embodiments, a compound of formula I and ceftaroline, or a salt and/or solvate and/or prodrug thereof may be administered conjointly, such as simultaneously, for example, in one composition. In other embodiments, the two drugs may be administered sequentially. In some embodiments, a compound of formula I and ceftaroline, or a salt and/or solvate and/or prodrug thereof may be administered in singular dose. In other embodiments, a compound of formula I and ceftaroline, or a salt and/or solvate and/or prodrug thereof may be administered in two to six divided doses for example, every 4 hours, 6 hours, 8 hours or 12 hours.

A compound of formula I and ceftaroline, or a salt and/or solvate and/or prodrug thereof may be administered in therapeutically effective dosages, which may vary according to the type of infection, the patient in question, the administration route and the antibacterial agent. A compound of formula I and ceftaroline, or a salt and/or solvate and/or prodrug thereof may be administered non-orally or orally, for example, as injectable preparations, capsules, tablets or granular preparations.

In exemplary embodiments, the compound of formula I and ceftaroline, or a salt and/or prodrug thereof are administered parenterally (e.g., by IV or IM administration). In each case, in additional embodiments, the dosage form is administered parenterally (e.g., intravenously, intramuscularly) as a solution or suspension in a solvent, such as water, physiological saline, about a 5% to about 10% sugar (e.g., glucose, dextrose) solution, and combinations thereof.

For intramuscular administration of higher doses, the injection may occur at two or more intramuscular sites.

In exemplary embodiments, the present invention provides methods of treating bacterial infections comprising administering a composition comprising (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate or a pharmaceutically acceptable salt or a solvate thereof. The methods include, but are not limited to, administering any one of the compositions as described above. The bacterial infections include, but are not limited to, complicated skin and skin structure infections (cSSSI); community acquired pneumonia (CAP); complicated intra-abdominal infections, such as, complicated appendicitis, peritonitis, complicated cholecystitis and complicated diverticulitis; uncomplicated and complicated urinary tract infections, such as, pyelonephritis; and respiratory and other nosocomial infections. In some examples, the bacterial infection is community acquired pneumonia. In other embodiments, the bacterial infection is complicated skin and skin structure infection. In still other embodiments, the bacterial infection is complicated urinary tract infection.

In exemplary embodiments, the methods include administering a composition comprising a crystalline form of (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicyclo[4.2.0]oct-2-ene-2-carboxylate or a pharmaceutically acceptable salt or a solvate thereof. In some embodiments, the crystalline form may be characterized by a X-ray powder diffraction pattern comprising a characteristic peak at about 7.6, about 9.6, about 19.8, about 20.6, about 21.9, about 23.0 or about 24.3±0.2 degrees 2θ. In exemplary embodiments, the crystalline form is characterized by a X-ray powder diffraction pattern comprising one or more characteristic peaks at about 7.6, about 9.6, about 19.8, about 20.6, about 21.9, about 23.0 and about 24.3±0.2 degrees 2θ.

DEFINITIONS

Unless defined otherwise, all technical and scientific terms used herein generally have the same meaning as commonly understood by one of ordinary skill in the art to which this invention belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, and preferably up to 10% of a given value.

The term "effective amount" means the amount of the dosage form, which when administered to a patient (e.g., a mammal) for treating a disease, contains sufficient active ingredient to effect such treatment for the disease, so as to achieve the objectives of the invention. The "effective amount" will vary depending on the compound, the disease and its severity and the age, weight, physical condition and responsiveness, etc., of the patient to be treated.

The term "treating" means to relieve, alleviate, delay, reduce, reverse, improve, manage or prevent at least one symptom of a condition in a subject. The term "treating" may also mean to arrest, delay the onset (i.e., the period prior to clinical manifestation of a disease) and/or reduce the risk of developing or worsening a condition.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts may be prepared by reaction of a compound with the appropriate inorganic or organic acid via any of a number of known methods. Alternatively, alkali and alkaline earth metal salts can be prepared by reacting a compound with the appropriate base via a variety of known methods. The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

In certain embodiments, the pharmaceutically acceptable salt is a hydrochloride salt.

The term "prodrug" means a compound that is a drug precursor which upon administration to a subject undergoes chemical conversion by metabolic or chemical processes to yield a compound an active moiety. Suitable prodrugs of ceftaroline include, e.g., ceftaroline fosamil acetate and ceftaroline fosamil.

Solvates of a compound may form when a solvent molecule(s) is incorporated into the crystalline lattice structure of the compound molecule during, for example, a crystallization process. Suitable solvates of compounds of formula I include, but are not limited to, hydrates (monohydrate, sesquihydrate, dihydrate), solvates with organic compounds (e.g., $CH_3CO_2H$, $CH_3CH_2CO_2H$, $CH_3CN$), and combinations thereof.

As used herein the term "halogen" means F, Cl, Br, and I.

The term "alkyl" means a substituted or unsubstituted saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include, but are not limited to, 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by, e.g., halogen, hydroxyl, amino, carboxy, alkylamino, dialkylamino, aryl, heteroaryl, alkoxy, nitro, thio and cyano, and combinations thereof.

The term "halogenated alkyl" means a saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms, that is substituted by one or more halogens, such as, but not limited to, —$CF_3$, $CF_2CF_3$, $CHF_2$, $CH_2F$, and the like. The use of the term "halogenated alkyl" should not be construed to mean that a "substituted alkyl" group may not be substituted by one or more halogens.

The term "alkenyl" means a substituted or unsubstituted hydrocarbon radical which may be straight-chain or branched-chain, which contains one or more carbon-carbon double bonds, and which may comprise about 1 to about 20 carbon atoms, such as 1 to 12 carbon atoms, for instance 1 to 6 carbon atoms. Suitable alkenyl groups include ethenyl, propenyl, butenyl, etc.

Substituted alkenyl groups are alkenyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

The term "alkynyl" means a substituted or unsubstituted aliphatic hydrocarbon radical which may be straight-chain or branched-chain and which contains one or more carbon-carbon triple bonds. Preferably the alkynyl group contains 2 to 15 carbon atoms, such as 2 to 12 carbon atoms, e.g., 2 to 8 carbon atoms. Suitable alkynyl groups include ethynyl, propynyl, butynyl, etc.

Substituted alkynyl groups are alkynyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "amino" means —$NH_2$.

The term "alkylamino" means —H(alkyl), wherein alkyl is as described above.

The term "dialkylamino" means —$N(alkyl)_2$, wherein alkyl is as described above.

The term "aryl" means a substituted or unsubstituted aromatic monocyclic or bicyclic ring system comprising about 5 to about 14 carbon atoms, e.g., about 6 to about 10 carbon atoms. Suitable aryl groups include, but are not limited to, phenyl, naphthyl, anthracenyl.

Substituted aryl groups include the above-described aryl groups which are substituted one or more times by, for example, but not limited to, halogen, hydroxyl, amino, carboxy, alkylamino, dialkylamino, aryl, heteroaryl, alkoxy, nitro and cyano, and combinations thereof.

The term "arylamino" means —NH(aryl), wherein aryl is as described above.

The term "diarylamino" means —$N(aryl)_2$, wherein aryl is as described above.

The term "amido" means —$CONH_2$.

The term "aminoalkyl" means a -(alkylene)-amino, -(alkylene)-alkylamino or -(alkylene)-dialkylamino group, wherein the various groups are as described above.

The term "arylalkyl" refers to an -(alkylene)-aryl group in which the aryl and alkylene portions are in accordance with the previous descriptions. Suitable examples include, but are not limited to, benzyl, 1-phenethyl, 2-phenethyl, phenpropyl, phenbutyl, phenpentyl, and napthylmethyl.

The term "carboxyl" means —C(O)OH.

The term "cycloalkyl" means a monocyclic, bicyclic or tricyclic nonaromatic saturated hydrocarbon radical having 3 to 10 carbon atoms, such as 3 to 8 carbon atoms, for example, 3 to 6 carbon atoms. Suitable cycloalkyl groups include, but are not limited to, cyclopropyl, cyclobutyl, cyclopentyl, cyclohexyl, cycloheptyl, cyclooctyl, norbornyl, 1-decalin, adamant-1-yl, and adamant-2-yl. Other suitable cycloalkyl groups include, but are not limited to, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, and spiro[3.5]nonyl. Preferred cycloalkyl groups include cyclopropyl, cyclobutyl, cyclopentyl and cyclohexyl. The cycloalkyl group can be substituted, for example, by one or more halogens and/or alkyl groups.

The term "cycloalkylalkyl" means a -(alkylene)-cycloalkyl in which the cycloalkyl group is as previously described; e.g., cyclopropylmethyl, cyclobutylmethyl, cyclopentylethyl, or cyclohexylmethyl, and the like.

The term "heteroaryl" means a substituted or unsubstituted aromatic monocyclic or multicyclic ring system comprising 5 to 14 ring atoms, preferably about 5 to about 10 ring atoms and most preferably 5 or 6 ring atoms, wherein at least one of the ring atoms is an N, O or S atom. Suitable heteroaryl groups include, but are not limited to furyl, thienyl, pyrrolyl, pyrazolyl, imidazolyl, pyridyl, pyrimidinyl, benzimidazolyl, indazolyl, indolyl, quinolinyl, isoquinolinyl, naphthyridinyl and the like.

Substituted heteroaryl groups include the above-described heteroaryl groups which are substituted one or more times by, for example, but not limited to, halogen, hydroxyl, amino, carboxy, alkylamino, dialkylamino, aryl, heteroaryl, alkoxy, nitro and combinations thereof.

The term "heteroarylalkyl" refers to a -(alkylene)-heteroaryl group wherein the heteroaryl and alkylene portions are in accordance with the previous discussions. Suitable examples include, but are not limited to, pyridylmethyl, thiazolylmethyl, thienylmethyl, pyrimidinylmethyl, pyrazinylmethyl, and isoquinolinylmethyl, and the like.

The term "heterocycle" means a substituted or unsubstituted non-aromatic mono- or multicyclic ring system comprising 3 to 10 atoms, preferably 5 or 6, wherein at least one of the ring atoms is an N, O or S atom. Suitable heterocyle groups include, but are not limited to tetrahydrofuranyl, tetrahydrothienyl, tetrahydropyranyl, dihydropyranyl, pyrrolidinyl, piperidinyl, piperazinyl, thiomorpholinyl, morpholinyl, isoxazolinyl, and the like.

Substituted heterocycle groups include the above-described heterocycle groups which are substituted one or more times by, for example, halogen, amino, alkyl, hydroxy, carboxy, and combinations thereof. Heterocycle groups may also be substituted by, e.g., aryl or heteroaryl.

The term "heterocyclealkyl" refers to a -(alkylene)-heterocycle group wherein the heterocycle and alkylene portions are in accordance with the previous discussions.

The term "aroyl" means an aryl-C(O)—, in which the aryl group is as previously described. Suitable aroyl groups include, but are not limited to, benzoyl and 1-naphthoyl.

The term "acyl" means an HC(O)—, alkyl-C(O)—, cycloalkyl-C(O)—, aryl-C(O)—, or heteroalkyl-C(O)—, in which the various groups are as previously described, e.g., acetyl, propionyl, benzoyl, pyridinylcarbonyl, and the like.

The term "alkoxy" means alkyl-O— groups in which the alkyl portion is in accordance with the previous discussion. Suitable alkoxy groups include, but are not limited to, methoxy, ethoxy, n-propoxy, iso-propoxy, n-butoxy, t-butoxy, pentoxy, hexoxy, heptoxy, octoxy, and the like. For example, the alkoxy can be methoxy or ethoxy.

The term "aryloxy" means an aryl-O— group, in which the aryl group is as previously described.

The term "heteroaryloxy" means an heteroaryl-O— group, in which the heteroaryl group is as previously described.

The term "cycloalkylalkyloxy" means a —O-(alkylene)-cycloalkyl group, in which the cycloalkyl and alkylene groups are as previously described.

The term "thio" means —SH.

The term "alkylthio" means an alkyl-S— group, in which the alkyl group is as previously described.

The term "arylthio" means an aryl-S— group, in which the aryl group is as previously described.

The term "alkylsulfinyl" means a —SOR radical where R is alkyl as defined above, e.g., methylsulfinyl, ethylsulfinyl, and the like.

The term "alkylsulfonyl" means a —SO$_2$R radical where R is alkyl as defined above, e.g., methylsulfonyl, ethylsulfonyl, and the like.

The term "arylsulfinyl" means a —SOR radical where R is aryl as defined above, e.g., phenylsulfinyl, and the like.

The term "arylsulfonyl" means a —SO$_2$R radical where R is aryl as defined above, e.g., phenylsulfonyl, and the like.

The term "heteroarylsulfinyl" means a —SOR radical where R is heteroaryl as defined above.

The term "heteroarylsulfonyl" means a —SO$_2$R radical where R is heteroaryl as defined above.

The term "alkoxycarbonyl" means an alkyl-O—C(O)— group, in which the alkyl group is as previously described.

The term "aryloxycarbonyl" means an aryl-O—C(O)— group, in which the aryl group is as previously described.

The term "heteroaryloxycarbonyl" means an heteroaryl-O—C(O)— group, in which the heteroaryl group is as previously described.

The term "cycloalkyloxy" means a —O-cycloalkyl group in which the cycloalkyl group is as previously described, e.g., cyclopropyloxy, cyclobutyloxy, cyclopentyloxy, cyclohexyloxy, and the like.

The term "arylalkyloxy" means —O-(alkylene)-aryl group, in which the aryl and alkylene groups are as previously described.

The term "heteroarylalkyloxy" means —O-(alkylene)-heteroaryl group, in which the heteroaryl and alkylene groups are as previously described.

EXAMPLES

The present invention will now be further described by way of the following non-limiting examples. In applying the disclosure of these examples, it should be kept clearly in mind that the examples are merely illustrative of the present invention and should not be construed as limiting the scope of the invention in any way as many variations and equivalents that are encompassed by the present invention will become apparent to those skilled in the art upon reading the present disclosure.

Ceftaroline fosamil may be prepared as described, for example, in U.S. Pat. No. 6,417,175. Ceftaroline fosamil acetate may be prepared as described, for example, in U.S. Pat. No. 6,906,055. (6R,7R)-7-[[(2Z)-2-(ethoxyimino)-2-[5-(amino)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicyclo[4.2.0]oct-2-ene-2-carboxylate may be prepared as described, for example in Japanese Patent No. JP 09100283.

X-Ray Powder Diffractometry (XRD)

A small amount of sample is loaded on a zero background holder and exposed to CuKa radiation (30 kV×15 mA) in a wide-angle bench-top X-ray diffractometer (Model Mini-Flex, Rigaku/MSC Inc., Woodlands, Tex.). The instrument is operated in the step-scan mode, in increments of 0.05° 2θ. The angular range is 2 to 40° 2θ, and the scan rates range from 0.5-1° 2θ/min. The data collection and analyses are performed with commercially available software (JADE, version 7.1, Materials Data, Inc., Livermore, Calif.).

Example 1

Synthesis of (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate hydrochloride Acetyl chloride (129.90 g, 1654.77 mmol) and pyridine (23.47 g, 296.67 mmol) were added to a solution of (6R,7R)-7-[[(2Z)-2-(ethoxyimino)-2-[5-(amino)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate (100 g, 164.82 mmol) in dimethylacetamide (1300 ml) and the resulting mixture was stirred at 0-5° C. for 4 to 6 hours. The reaction mixture was then poured into excess acetone to form a slurry which was filtered and dried at room temperature overnight in vacuo to afford 97 g of crude (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicyclo[4.2.0]oct-2-ene-2-carboxylate. 63% purity by HPLC area % assay (Luna 3 micron C18, 3.0 mm×50 mm; NH$_4$OAc/CH$_3$CN; 1.0 ml/min flow rate)

Purification Procedures

The crude product (97 g) was purified by resin chromatography (elution with water followed by 5-15% acetonitrile in water) to provide clean fractions (>90% HPLC purity). The excess solvents were removed by lyophilization which afforded about 34 g (35% yield) of product which was found to be 85-87% pure by HPLC assay method (Luna 3 micron C18, 3.0 mm times 50 mm; $NH_4Ac/CH_3CN$; 1.0 ml/min flow rate). Repeated triturations (for example, three times) with acetonitrile/1% HCl (95:5) resulted in 31 g of purified material that was analyzed by HPLC as 98.5% pure. This material was then subjected to prep-LC purifications using an isocratic HPLC method (ONDAPAK® column, 3.9 mm times.300 mm, 14% acetonitrile in water, 2 ml/min flow rate) to afford (6R,7R)-7-[[(2Z)-2-(ethoxyimino)-2-[5-(acetamido)-1,2,4-thiadiazol-3-yl] a-cetyl]amino]-3-[[4-(1-methylpyridinium-4-yl)-1,3-thiazol-2-yl]sulfanyl]-8-oxo-5-thia-1-azabicylo[4.2.0] oct-2-ene-2-carboxylate hydrochloride in purity of greater than 95% that was used for the pharmacological and toxicological studies described below.

Mass spectral peak positions for the product are shown in Table 4. The peak at 647.1 represents the nominal mass. Other peaks that occur at 648.1, 649.0, 650.1, 651.1, and 652 are due to presence of isotopic carbon, oxygen, sulfur and hydrogen atoms present in the compound.

TABLE 4

Isotropic Distribution of Compound A

| m/z (amu) | Relative Intensity |
| --- | --- |
| 647.1 | 100 |
| 648.1 | 33.3 |
| 649.0 | 24.3 |
| 650.1 | 6.72 |
| 651.1 | 2.50 |
| 652.0 | 0.60 |
| 653.1 | 0.14 |
| 654.1 | 0.03 |
| 655.1 | 0.005 |
| 656.1 | 0.0007 |
| 657.1 | 0.0001 |
| 658.0 | 0 |

Peak positions for the X-ray powder diffraction pattern in FIG. 1 are provided in Table 5.

TABLE 5

X-Ray Powder Diffraction Pattern Peaks

| 2θ (°) | Height |
| --- | --- |
| 5.841 | 73 |
| 7.579 | 263 |
| 9.56 | 379 |
| 11.599 | 151 |
| 12.478 | 116 |
| 13.7 | 165 |
| 15.219 | 168 |
| 16.999 | 87 |
| 17.263 | 73 |
| 17.944 | 107 |
| 18.921 | 201 |
| 19.8 | 302 |
| 20.581 | 379 |
| 21.341 | 131 |
| 21.881 | 323 |
| 23.021 | 321 |
| 24.258 | 407 |
| 24.995 | 71 |
| 26.261 | 238 |
| 27.381 | 139 |
| 29.929 | 58 |
| 30.125 | 94 |
| 30.538 | 172 |
| 31.557 | 67 |
| 34.092 | 56 |
| 36.174 | 66 |
| 38.18 | 79 |
| 39.343 | 83 |

Example 2 pH Solubility Profile of Compound A

The solubility of Compound A was measured at room temperature by adding an excess of Compound A to different USP buffers with pH ranging from 1.1 to 9.4. Testing was conducted using a reciprocating platform shaker (Heidolph® Promax 1020). The results are shown in Table 6.

TABLE 6 pH Solubility Profile of Compound A

| pH | Approximate Solubility (mg/ml) | Description |
| --- | --- | --- |
| pH 1.0 (0.2 M KCl—HCl) | 0.5 | Solution |
| pH 3.0 (0.1 M Sodium acetate) | 4.7 | Solution |
| pH 5.0 (0.05 M Sodium acetate) | 0.8 | Gel |
| pH 5.0 (0.1 M Sodium acetate) | 0.4 | Gel |
| pH 5.0 (0.5 M Sodium acetate) | 0.5 | Gel |
| pH 7.0 (0.1 M Potassium Phosphate) | 0.4 | Gel |
| pH 9.0 (0.1 M Potassium phosphate) | 13.3 | Solution |

The solubility of Compound A in various solvent mixtures is shown in Table 7.

TABLE 7

Solubility of Compound A in Solvent Mixtures

| Solvent Mixture | Approximate Solubility (mg/ml) |
| --- | --- |
| 8% Propylene Glycol, 9% PEG-300, 83% Acetate buffer pH 5 (1M) | 1.1 |
| 8% Propylene Glycol, 2% Ethanol, 90% Acetate buffer pH 5 (1M) | 1.5 |
| 8% Propylene Glycol, 2% Ethanol, 5% Benzyl alcohol, 85% Acetate buffer pH 5 (1M) | 1.5 |
| 8% Propylene Glycol, 2% Ethanol, 2% PEG-300, 88% Acetate buffer pH 5 (1M) | 1.8 |
| 8% Propylene Glycol, 2% Ethanol, 2% PEG-300, 5% 1-Methyl-2-pyrrolidinone, 83% Acetate buffer pH 5 (1M) | 2.0 |
| 8% Propylene Glycol, 2% Ethanol, 5% Benzyl alcohol, 85% Acetate buffer pH 5 (1M) | 3.5 |
| 8% Propylene Glycol, 2% PEG-300, 5% Benzyl alcohol, 85% Acetate buffer pH 5 (1M) | 4.0 |
| 40% Propylene Glycol, 2.5% Ethanol, 57.5% Acetate buffer pH 5 | 4.2 |
| 60% Propylene Glycol, 2.5% Ethanol, 37.5% Acetate buffer pH 5 | >25 |
| 10% Sodium benzoate in water, pH 6.3 | 4.2 |
| 10% Sodium benzoate in Normal Saline, pH 6.5 | 4.2 |
| Sterile water for injection USP | 0.8 |

TABLE 7-continued

Solubility of Compound A in Solvent Mixtures

| Solvent Mixture | Approximate Solubility (mg/ml) |
|---|---|
| Ethanol | 1.5 |
| Methanol | 400 |
| Dimethyl sulfoxide (DMSO) | 212 |

Example 3

Preparations of Dosage Forms Containing Compound A Suitable for Parenteral Administration An example of a dosage form containing 4.20 mg/ml of Compound A that is suitable for parenteral (e.g., IM or IV) administration is provided in Table 8.

TABLE 8

Dosage Form Containing Compound A

| Ingredient | Amount per 120 ml |
|---|---|
| Compound A | 558 mg* |
| Propylene Glycol, USP | 28.8 ml |
| Ethanol 95%, USP | 7.20 ml |
| PEG-300, USP/NF | 36.0 ml |
| Acetate buffer (pH 5.0, 1M) | q.s. to 120 ml |

*corrected for purity (factor of 0.95) and free base/HCl salt ratio (factor of 0.95)

The propylene glycol, PEG-300 and ethanol were added to a volumetric flask and mixed. The acetate buffer pH 5.0 (1M) was then added q.s to volume and the contents of the flask were mixed. Compound A was added to a separate clear dry volumetric flask. Approximately ⅓ of the total propylene glycol, PEG-300 and ethanol mixture was added and the resulting mixture was shaken vigorously for 2 minutes. The remainder of the mixture was then added to the flask to make up the volume. The contents were mixed by gentle shaking or by sonication until a clear solution was obtained. The solution was then filtered through a 0.22µ filter (Millex® GV) using a sterile disposable syringe or vial.

The stability of this solution at room temperature is shown in Table 9.

TABLE 9

Room Temperature Stability

| Batch | Initial pH | Initial Assay (%) | Final pH | Final Assay (%) |
|---|---|---|---|---|
| 1 | 6.06 | 99.2 | — | — |
| 2 | 6.06 | 101.3 | — | 97.9 (5 hrs at RT) |
| 3 | 6.08 | 100.5 | — | 95.6 (5 hrs at RT) |
| 4 | 6.13 | 98.5 | 5.99 | 96.9 (3 hrs at RT) |

An example of a dosage form containing 1.0 mg/ml of Compound A hydrochloride that is suitable for parenteral (e.g., IM or IV) administration is provided in Table 10.

TABLE 10

Parenteral Dosage Form

| Ingredient | Amount (mg/batch) |
|---|---|
| Compound A hydrochloride | 27.6 |
| L-arginine | 543.3 |
| Normal Saline for Injection USP | q.s. to 25 ml |
| 0.05 N HCl | q.s |

The L-arginine was dissolved in saline and the pH of the solution was adjusted to ~8.0 using 0.05N HCl. Compound A was then added and the pH of the solution was adjusted to ~7.40. The solution was then filtered through a 0.22 µm filter. The stability of this solution at room temperature is shown in Table 11.

TABLE 11

Room Temperature Stability

| Time | pH | % Assay |
|---|---|---|
| Initial | 7.35 | 95.7 |
| 2 hours | 7.34 | 95.3 |
| 4 hours | 7.41 | 95.1 |

As can be seen in Table 11, the solution containing 1 mg/ml of Compound A is stable and is therefore suitable for infusion administration.

Example 4

Preparation of Formulations Containing Compound a and Ceftaroline Fosamil Suitable for Parenteral Administration Examples of dosage forms containing Compound A hydrochloride and ceftaroline fosamil that are suitable for parenteral (e.g., IM or IV) administration are provided in Table 12.

TABLE 12

Dosage Forms

| Component | Formulation #1 | Formulation #2 | Formulation #3 |
|---|---|---|---|
| Ceftaroline fosamil | 600 mg | 600 mg | 600 mg |
| Arginine | 440 mg | 440 mg | 440 mg |
| Compound A hydrochloride | 6 mg | 15 mg | 18 mg |
| Normal Saline for Injection USP | 20 ml | 20 ml | 20 ml |

600 mg of ceftaroline fosamil and 440 mg of arginine were added to 20 ml of normal saline for injection USP. The solution was allowed to stand at ambient temperature for 5 minutes then Compound A was added. The resulting solution was again allowed to stand at ambient temperature for 5 minutes. The final solution was filtered through a 0.24 membrane filter (Millex® GV) and stored in a sterile vial.

The stability of Formulations 1-3 of Table 12 at room temperature is shown in Tables 13-15.

TABLE 13

Stability of Formulation 1

| Time | pH | Compound A Assay (%) | Ceftaroline Fosamil Assay (%) |
|---|---|---|---|
| Initial | 5.41 | 105.6 | 107.4 |
| 2 hr | 5.46 | 105.5 | 108.0 |
| 4 hr | 5.32 | 104.5 | 105.8 |

Ceftaroline fosamil concentration: 30 mg/ml
Compound A concentration: 0.30 mg/ml

TABLE 14

Stability of Formulation 2

| Time | pH | Compound A Assay (%) | Ceftaroline Fosamil Assay (%) |
|---|---|---|---|
| Initial | 5.36 | 95.4 | 105.9 |
| 2 hr | 5.33 | 95.4 | 106.1 |
| 4 hr | 5.28 | 94.5 | 104.4 |

Ceftaroline fosamil concentration: 30 mg/ml
Compound A concentration: 0.75 mg/ml

TABLE 15

Stability of Formulation 3

| | Time | pH | Compound A Assay (%) | Ceftaroline Fosamil Assay (%) |
|---|---|---|---|---|
| Batch 1 | Initial | 5.37 | 102.7 | 96.0 |
| | 4 hr | 5.34 | 104.6 | 94.2 |
| Batch 2 | Initial | 5.54 | 102.6 | 94.9 |
| | 4 hr | 5.57 | 104.2 | 92.7 |

Ceftaroline fosamil concentration: 30 mg/ml
Compound A concentration: 0.90 mg/ml As can be seen from Tables 13-15, Formulations 1-3 are stable for at least 4 hours at room temperature, and may therefore be used, e.g., for infusions in human patients at room temperature. A formulation similar to Formulations 1-3, but having a ceftaroline concentration of 30 mg/ml and a Compound A concentration of 2.25 mg/ml was found to be stable for at least 10 minutes at room temperature and thus can used intramuscularly.

Example 5

Toxicity Testing

The potential toxicity of an intravenously administered formulation of Compound A (average concentration analysis=95.6%) was studied for four weeks in rats (CD® strain). The vehicle (L-arginine dissolved in saline, 21.7 mg/ml), control (saline solution) and test solutions were administered by an intravenous infusion in the cannulated femoral vein through a dosing port. The dose was administered once per day at approximately the same time (±2 hours) each day throughout the duration of the study. The dose volume was 10 ml/kg per day. All doses were administered using a syringe infusion pump set for the appropriate infusion rate to deliver the proper dose volume over the required infusion duration of 15 minutes. All animals across all groups were examined prior to exposure and all the main study survivors were examined again at the end of study. All animals were observed at least twice a day for morbidity, mortality, injury, and availability of food and water. Detailed clinical examinations were made for each animal daily during treatment (approx 30 to 60 minutes post-dosing).

The results of the toxicological profile are given in Table 16.

TABLE 16

Toxicity Testing

| Test Compound | No. of Animals | Day 1 | Day 7 | Day 14 | Day 21 | Day 28 |
|---|---|---|---|---|---|---|
| Compound A (9 mg/kg/day) | 42 | No adverse clinical signs observed | No adverse clinical signs observed | No adverse clinical signs observed | No adverse clinical signs observed | No adverse clinical signs observed |
| Control (Saline) and Vehicle | 28 | No adverse clinical signs observed | No adverse clinical signs observed | No adverse clinical signs observed | No adverse clinical signs observed | No adverse clinical signs observed |

The control and vehicle were administered separately (i.e., as two different study groups).

As can be seen from Table 16, Compound A (administered at a dose of 9 mg/kg/day) did not show any adverse clinical events over a period of 28 days.

Genotox Studies on Compound A Hydrochloride

In vitro genotoxicity studies were conducted as a mouse lymphoma study and a chromosomal aberration test. The vehicle was DMSO and the maximum concentration to be tested was 5000 µg/ml for both studies.

[A] In Vitro Mammalian Cell Gene Mutation Test (L5178Y/TK$^{+/-}$ Mouse Lymphoma Assay)

The purpose of this study was to evaluate the genotoxic potential of the test article based on quantitation of forward mutations at the thymidine kinase locus of L5178Y mouse lymphoma cells and the sizing of the resulting colonies.

Controls:
Negative: Test article solvent (or vehicle)
Positive: Methyl methanesulfonate (MMS)
7,12-dimethylbenz(a)anthracene (DMBA)

[B] In Vitro Mammalian Chromosome Aberration Test

The purpose of this study was to evaluate the clastogenic potential of a test article based upon its ability to induce chromosome aberrations in human peripheral blood lymphocytes (HPBL).

Controls:
Negative: Test Article Solvent (or Vehicle)
Positive: Mitomycin C (MMC, CAS number 50-07-7)
Cyclophosphamide (CP, CAS number 6055-19-2)

Results from both genotoxicity studies (mouse lymphoma and chromosomal aberration study using human lymphocytes) conducted on purified compound A material were negative.

Example 6

Anti-Bacterial Activity

The antibiotic activity of Compound A (as the hydrochloride salt) was tested by Agar Diffusion against the following bacterial strains: *Staphylococcus aureus, Salmonella typhimurium, Escherichia coli* and *Pseudomonas aureus*. The antibiotic activity of Compound A was compared to that observed for the antibiotic gentamicin (positive control antibiotic). 0.85% saline solution was used as a negative control. The protocol is provided below.

A solution containing Compound A hydrochloride, 20 ug per disk, was added to BBL™ Sensi-Disc™. Fifteen Petri dish filled with an agar medium were prepared a day before their use. These were utilized for testing of 5 microorganisms (4 bacterial species including *Staphylococcus aureus, Salmonella typhimurium, Pseudomonas aeruginosa*, and *Escherichia coli*, and one fungus (*Candida albicans*). Triplicate plates were then streaked with each specific microorganism. Twelve plates to be utilized for antibacterial testing were applied with positive control and negative control discs. Positive control discs are impregnated with gentamycin and are available from Becton, Dickinson and Co (ready to be used cartridges, "BBL™ Sensi-Disc™ Antimicrobial Susceptibility Test Discs"). Negative control discs were prepared by soaking dry disks with normal saline solution. These discs were applied by means of a BBL™ dispenser, using aseptic precautions. The remaining (three) plates to be utilized for antifungal properties were also applied with positive and negative controls; however, in this case positive control discs were impregnated with nystatin (available as BBL™ Taxo™ Nystatin Discs Cartridge from BD & Co). Fifteen dry discs (identical to those of positive and negative control discs but with unique identification print on one side, "NY") were soaked with a solution of Compound A hydrochloride for about 5 minutes. The discs were then carefully transferred (using a sterile forceps) to a sterile empty Petri dish to decant off any excess test solution. Then one disc was applied to each of fifteen plates that were previously applied with positive and negative controls. The approximate loading of compound A was 22 µg/disk. Triplicate plates for each microorganism were assembled together and properly labeled prior to incubation. Plates for antibacterial testing were incubated at 30-35° C. (for 2 days) while for antifungal testing plates were incubated at 24° C. Plates were read for zones of inhibition using Vernier calipers.

The results are shown in Table 17.

TABLE 17

Antibacterial Activity

| | Zone of Inhibition (mm) (average of 3 plates) | | | |
|---|---|---|---|---|
| Test Sample | *Staphylococcus aureus* | *Salmonella typhimurium* | *Escherichia coli* | *Pseudomonas aureus* |
| Compound A hydrochloride | 36.71 | 21.12 | 23.82 | 9.68 |
| Gentamicin (positive control) | 21.27 | 18.03 | 20.27 | 20.17 |
| 0.85% saline solution (negative control) | None | None | None | None |

As can be seen from Table 17, Compound A hydrochloride shows surprisingly and unexpectedly higher antibacterial activity than Gentamicin (10 mcg per disk) in *Staphylococcus aureus* (173%), *Salmonella typhimurium* (117%) and *Escherichia coli* (118%). Compound A hydrochloride has moderate activity against *Pseudomonas aureus*.

Example 7

In Vitro Metabolism

In vitro metabolism studies were performed to determine if compound A converts to ceftaroline, ceftaroline fosamil or the metabolite of ceftaroline, M1. The results are shown in the Table 18. As can be seen, the antibacterial activity of compound A is not due to its further metabolism to ceftaroline or metabolite M1.

TABLE 18

In Vitro Metabolism

| Compound A | | % of concentration of compound in media after incubation for 1 hour | | | |
|---|---|---|---|---|---|
| Concentration (ug/ml) | Medium | Compound A | Ceftaroline Fosamil | Ceftaroline | Ceftaroline metabolite M1 |
| 1 | S9 Fraction | 76 | ND | ND | ND |
| 10 | S9 Fraction | 68 | ND | ND | ND |
| 1 | Human Plasma | 32 | ND | ND | ND |
| 10 | Human Plasma | 81 | ND | ND | ND |

S9 contains a wide variety of enzymes catalyzed by hydrolysis, reduction, oxidation and conjugation, including P450 enzymes, flavin-monooxygenases, carboxylesterases, epoxide hydrolase, UDP-glucuronosyltransferases, sulfotransferases, methyltransferases, acetyltransferases, glutathione S-transferases and other drug-metabolizing enzymes. ND = not detected As can be seen from the Examples given above, compounds of formula I (e.g., Compound A) and pharmaceutically acceptable salts thereof, are surprisingly and unexpectedly safe and effective for the treatment of bacterial infections.

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalence in all respects.

The entire disclosures of all patents, patent applications and publications, cited herein, are hereby incorporated by reference.

What is claimed:

1. A compound of formula (I):

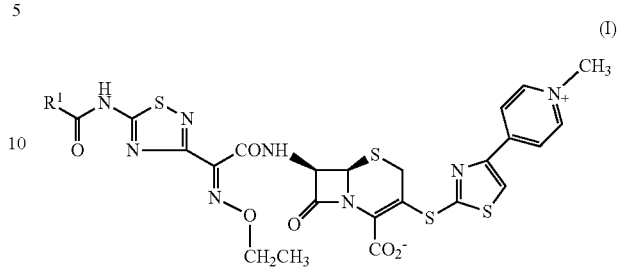

wherein

R$^1$ is hydrogen, alkyl, alkenyl, alkynyl, aryl, heteroaryl, heterocycle, —C(O)alkyl, —C(O)OH, —CH(NH$_2$)(CH$_2$)$_3$—NH—C(NH)NH$_2$ or —CH(NH$_2$)—CH$_2$—C(O)NH$_2$;

wherein, when present, any alkyl, aryl, heteroaryl or heterocycle group may optionally be substituted by halogen, hydroxyl, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, thio, alkylthio, arylthio, alkylsulfinyl, alkylsulfonyl, arylsulfinyl, arylsulfonyl, heteroarylsulfinyl, heteroarylsulfonyl, alkoxycarbonyl, aryloxycarbonyl or heteroaryloxycarbonyl;

or a pharmaceutically acceptable salt thereof.

2. A compound according to claim 1, wherein R$^1$ is hydrogen, alkyl or aryl.

3. A compound according to claim 1, wherein the compound is (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicyclo[4.2.0]oct-2-ene-2-carboxylate or a pharmaceutically acceptable salt thereof.

4. A pharmaceutical composition comprising a compound selected from the group consisting of ceftaroline, ceftaroline fosamil, ceftaroline fosamil acetate, and a pharmaceutically acceptable salt and/or a prodrug thereof and a compound according to claim 3.

5. A pharmaceutical composition comprising ceftaroline fosamil or ceftaroline fosamil acetate and a compound according to claim 3.

6. The pharmaceutical composition according to claim 5 comprising up to about 10 mg of (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicyclo[4.2.0]oct-2-ene-2-carboxylate or a pharmaceutically acceptable salt thereof.

7. The pharmaceutical composition according to claim 5 comprising up to about 5 mg of (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicyclo[4.2.0]oct-2-ene-2-carboxylate or a pharmaceutically acceptable salt thereof.

8. The pharmaceutical composition according to claim 5 comprising up to about 2.5 mg of (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicyclo[4.2.0]oct-2-ene-2-carboxylate or a pharmaceutically acceptable salt thereof.

9. The pharmaceutical composition according to claim 5 comprising up to about 1 mg of (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicyclo[4.2.0]oct-2-ene-2-carboxylate or a pharmaceutically acceptable salt thereof.

10. A method of treating a bacterial infection comprising administering to a patient in need thereof a composition according to claim 8.

11. A method of treating a bacterial infection comprising administering to a patient in need thereof a composition according to claim 9.

12. A crystalline form of (6R,7R)-7-[[(2Z)-2-(ethoxyimino)-2-[5-(acetamido)-1,2,4-thiadiazol-3-yl]acetyl]amino]-3-[[4-(1-methylpyridinium-4-yl)-1,3-thiazol-2-yl]sulfanyl]-8-oxo-5-thia-1-azabicylo[4.2.0]oct-2-ene-2-carboxylate hydrochloride] characterized by a X-ray powder diffraction pattern with CuK∞radiation comprising characteristic peaks at about 9.6, about 20.6, about 21.9, about 23.0 and about 24.3±0.2 degrees 2θ.

13. The method of claim 11 wherein the bacterial infection is selected from the group consisting of community acquired bacterial pneumonia and bacterial skin and skin structure infections.

14. The method of claim 13 wherein the pharmaceutical composition comprises 600 mg ceftaroline fosamil.

15. The method of claim 14 wherein the pharmaceutical composition is administered every 12 hours by intravenous infusion.

16. The method of claim 10 wherein the bacterial infection is selected from the group consisting of community acquired bacterial pneumonia and bacterial skin and skin structure infections.

17. The method of claim 16 wherein the pharmaceutical composition comprises 600 mg ceftaroline fosamil.

18. The method of claim 17 wherein the pharmaceutical composition is administered every 12 hours by intravenous infusion.

19. A method of treating a bacterial infection comprising administering to a patient in need thereof a pharmaceutical composition according to claim 7 wherein the bacterial infection is selected from the group consisting of community acquired bacterial pneumonia and bacterial skin and skin structure infections and the pharmaceutical composition comprises 600 mg ceftaroline fosamil.

20. The method of claim 13 wherein the pharmaceutical composition comprises 400 mg ceftaroline fosamil.

21. The method of claim 20 wherein the pharmaceutical composition is administered every 12 hours by intravenous infusion.

22. The method of claim 16 wherein the pharmaceutical composition comprises 400 mg ceftaroline fosamil.

23. The method of claim 22 wherein the pharmaceutical composition is administered every 12 hours by intravenous infusion.

* * * * *